(12) United States Patent
Radmer et al.

(10) Patent No.: US 9,017,292 B2
(45) Date of Patent: Apr. 28, 2015

(54) MEDICAL INJECTION DEVICE

(75) Inventors: Bo Radmer, Hilleroed (DK); Christian Plambech, Soeborg (DK); Christian Hoejris Nielsen, Copenhagen NV (DK); Jesper Peter Windum, Hilleroed (DK); Tom Hede Markussen, Bagsvaerd (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 13/977,083

(22) PCT Filed: Dec. 29, 2011

(86) PCT No.: PCT/EP2011/074255
§ 371 (c)(1),
(2), (4) Date: Sep. 19, 2013

(87) PCT Pub. No.: WO2012/089821
PCT Pub. Date: Jul. 5, 2012

(65) Prior Publication Data
US 2014/0025014 A1    Jan. 23, 2014

Related U.S. Application Data

(60) Provisional application No. 61/430,327, filed on Jan. 6, 2011.

(30) Foreign Application Priority Data

Dec. 31, 2010 (EP) .................................. 10197464

(51) Int. Cl.
*A61M 5/32* (2006.01)
*A61M 5/00* (2006.01)
*A61M 5/24* (2006.01)
*A61M 5/31* (2006.01)

(52) U.S. Cl.
CPC ............. *A61M 5/3202* (2013.01); *A61M 5/002* (2013.01); *A61M 5/2466* (2013.01); *A61M 2005/3117* (2013.01)

(58) Field of Classification Search
CPC ............. A61M 2005/3254; A61M 2005/3243; A61M 2005/208; A61M 2005/3267; A61M 5/2455; A61M 5/2466
USPC ......... 604/192, 197, 200–206, 223–233, 211, 604/241, 198; 206/364, 365
See application file for complete search history.

(56) References Cited

U.S. PATENT DOCUMENTS 3,158,155 A * 11/1964 Myerson et al. ............... 604/202
5,829,589 A   11/1998 Nguyen et al.
(Continued)

FOREIGN PATENT DOCUMENTS

DE    10203598 A1   8/2003
EP      279583 A2   8/1988
(Continued)

*Primary Examiner* — Bhisma Mehta
*Assistant Examiner* — Hamza Darb
(74) *Attorney, Agent, or Firm* — Wesley A. Nicolas; Reza Green; Richard W. Bork

(57) ABSTRACT

The present invention relates to injection devices for injecting a dose of a medicament. The injection device (100) incorporates a housing (101), a needle assembly (150) and a cover (200). The needle assembly (150) comprises an injection needle (152, 153) accommodated in a needle container (151) having an opening which in a storage state of the injection device (100) is sealed by a film seal (155). The cover may include sections (201, 202) arranged movable relative to the housing (101). The injection device (100) is so configured that upon movement of the cover sections (201, 202) relative to the housing (101) the film seal (155) is changed from a sealing state to an unsealing state for shifting the injection device (100) into a ready-to-administer state.

12 Claims, 6 Drawing Sheets

(56) References Cited

U.S. PATENT DOCUMENTS

Figure 1D:
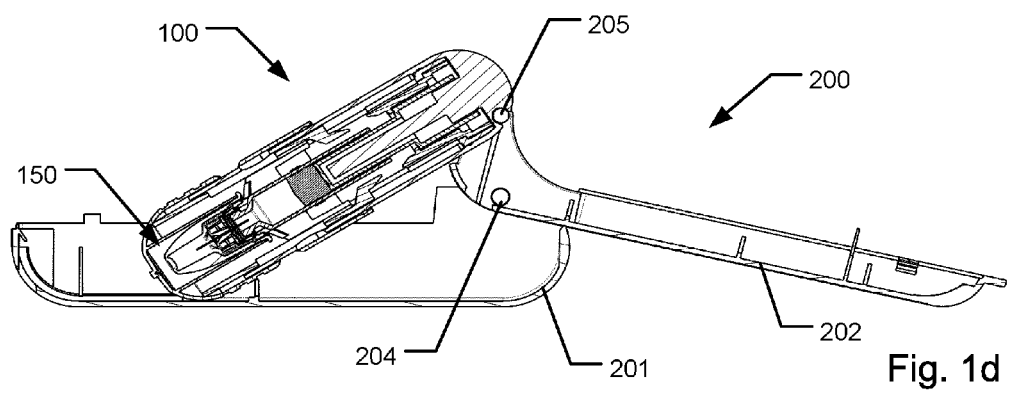

| | | |
|---|---|---|
| 5,928,205 A | 7/1999 | Marshall |
| 5,931,828 A * | 8/1999 | Durkee .................. 604/403 |
| 2003/0144633 A1 * | 7/2003 | Kirchhofer ............... 604/201 |
| 2006/0178631 A1 | 8/2006 | Gillespie et al. |

FOREIGN PATENT DOCUMENTS

| | | |
|---|---|---|
| EP | 1958654 A1 | 8/2008 |
| GB | 2447787 A | 9/2008 |
| WO | 96/02290 A1 | 2/1996 |
| WO | 01/07104 A1 | 2/2001 |
| WO | 03/045480 | 7/2003 |
| WO | 2004/004812 A1 | 1/2004 |
| WO | 2008/008694 A2 | 1/2008 |
| WO | 2009/016161 A1 | 2/2009 |
| WO | 2010/089589 A1 | 8/2010 |
| WO | 2012/022810 A2 | 2/2012 |

\* cited by examiner

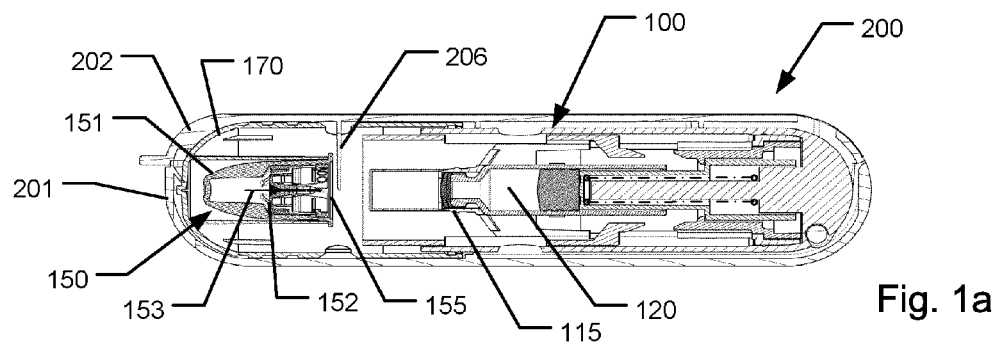
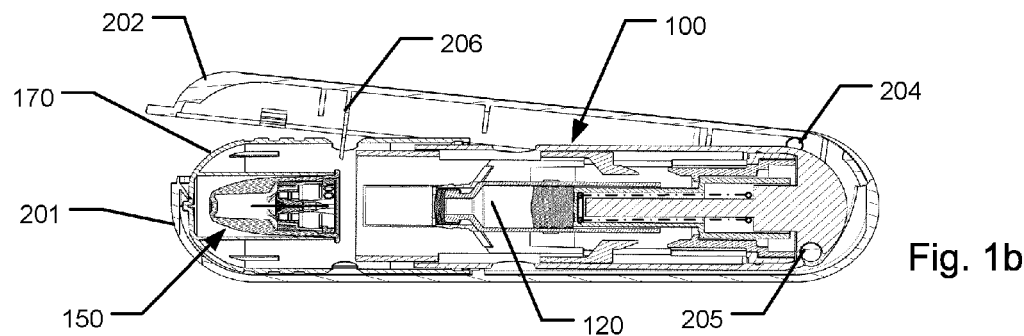
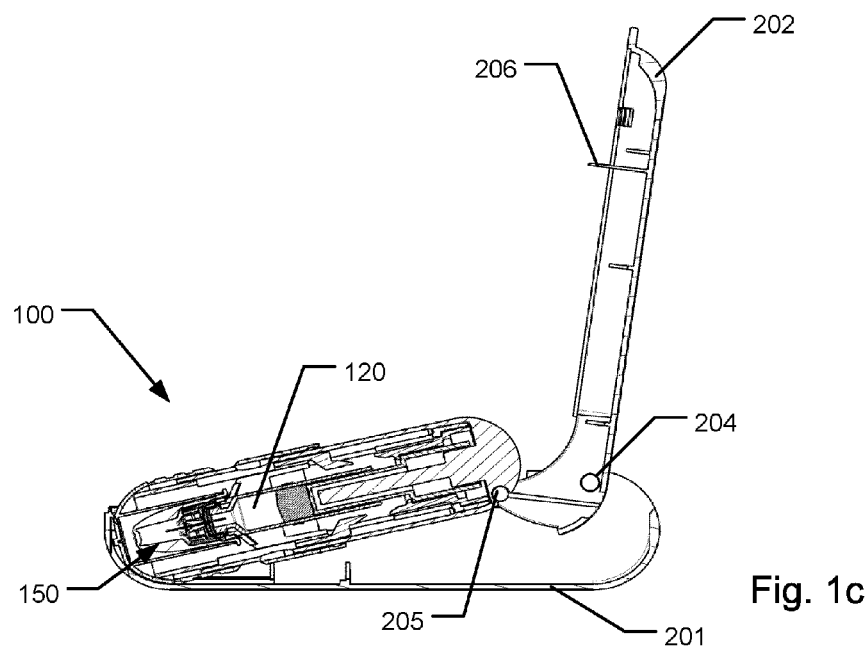
Fig. 1a
Fig. 1b
Fig. 1c

MEDICAL INJECTION DEVICE

CROSS-REFERENCE TO RELATED APPLICATIONS

This application is a 35 U.S.C. §371 National Stage application of International Application PCT/EP2011/074255 (WO 2012/089821), filed Dec. 29, 2011, which claimed priority of European Patent Application 10197464.0, filed Dec. 31, 2010; this application claims priority under 35 U.S.C. §119 of U.S. Provisional Application 61/430,327 filed Jan. 6, 2011.

FIELD OF THE INVENTION

The present invention relates to injection devices for injecting a medicament. In particular the present invention relates to single use injection devices for injecting a medicament from a held cartridge and improvements relating to the performance of such injection devices.

BACKGROUND OF THE INVENTION

In relation to some diseases patients must inject a medicament on a regular basis such as once weekly, once daily or even a plurality of times each day. In order to help patients overcome fear of needles, injection devices have been developed that involves auto-insertion of the needle which makes operation of an injection device as simple as possible. Such devices are typically designed as auto-injectors which provide automatic expelling of the medicament. In order to perform an injection, the user shall position the injection device onto the injection site and activate the device. Such activation causes the device to insert a needle into the skin, eject a dose of the medicament and subsequently move the needle into a shielded position.

For injection devices that use a cartridge without integrated injection needle, it is a requirement that the medicament container is connected to an injection needle in order for the medicament to be injected into the patient. The needle however must not be mounted prior to use as this will compromise the sterility of the needle and cartridge and could lead to contamination of both. The needle must therefore be mounted just before the device is used.

The procedure of mounting an injection needle to the device involves extensive handling of the needle which can result in unintentional needle cuts, contamination or damaging of the needle. Furthermore the needle handling can lead to users finding the device more difficult to use.

Designing the device to incorporate the needle will remove needle handling, however existing needles are difficult to use as internal needles, due to the design of their device interface, which typically requires a turning motion for mounting and their packaging comprising a needle container and a sterile barrier which under normal use are removed manually prior to mounting.

One example of an auto-injector incorporating an injection needle that is kept separate from the cartridge prior to use and which addresses the sterility issue is disclosed in WO 01/07104. In this reference, the needle assembly comprises two separate resilient needle sheaths for respectively protecting the front and rear needle. Typically, this type of needle sheath is made from latex rubber. During use, the needle sheaths are penetrated by the respective needle sections. Although ensuring sterility before use, the needle assemblies incorporating flexible needle sheaths typically leads to an increase in expenses during manufacture. In addition, mechanical impact during manufacture or during handling may lead to the sheaths becoming prematurely penetrated thereby compromising sterility of the injection needle.

U.S. Pat. No. 5,829,589 discloses a pen needle magazine dispenser to be received in a cap of a medication delivery pen. A plurality of cavities are formed in the dispenser. Each cavity accommodates a pen needle assembly. A disc shaped label or sterility barrier provides sterility for unused pen needle assemblies. Although the label is claimed to offer controlled breaking when an adaptor equipped delivery pen is pressed through the label the manual handling of the pen and the magazine dispenser does not provide for a user-friendly operation.

In a further reference, US2003/0144633 two example designs of a needle assembly are shown that involves a rear needle section of the injection needle that is kept in a sterile chamber by means of a film-type seal attached to the walls forming the chamber. The needle assembly is incorporated in an auto-injection device wherein a pre-stressed spring is used to drive forward a container and subsequently drive forward a piston of the container during the expelling operation. Upon triggering of the device, the container is driven forward so that the container penetrates through the film seal into the sterile chamber. This causes connection between container and the rear portion of the injection needle. The needle assemblies involve additional openings which necessitates use of further sealing members. Further, the particular designs of the disclosed needle assemblies are not particularly well-suited for use in connection with standard type injection devices, such as multi-use pen injectors where the needle handling is performed manually. This makes the manufacturing of the disclosed needle assemblies particular expensive. In addition, by using the one and same spring for facilitating both the penetration of the film-type seal as well as for injecting the medicament, an optimized operation of the two parts of the operation is very difficult to achieve.

Having regard to the above-identified prior art devices, it is an object of the present invention to provide an injection device incorporating a standard needle assembly of the conventional type used for multi-use pen injectors and which facilitates improved and consistent unsealing of the sealing member of the needle assembly.

Yet additional further objects of the invention are to provide measures for obtaining devices having a superior performance, providing easy operation and, at the same time, enabling manufacture at a reduced cost.

BRIEF DESCRIPTION OF THE INVENTION

In one aspect, the present invention relates to an injection device comprising:
a) a housing,
b) a cartridge arranged relative to the housing and defining a main axis, the cartridge comprising an outlet covered by a cartridge septum adapted to be pierced by an injection needle for establishing fluid communication with the cartridge interior and comprising a piston which is driveable along the main axis towards the outlet,
c) a piston driver for engaging the piston and capable of being actuated for driving the piston in a distal direction towards the outlet,
d) a needle assembly arranged at the distal end of the housing, the needle assembly comprising an injection needle having front and rear sections for respectively penetrating the skin of a subject user and for piercing the cartridge septum, the needle assembly further comprising a needle container accommodating the injection needle, the needle container having an opening which in an initial state of the injection device is sealed by a film seal for maintaining the injection needle in a sterile condition, and e) a cover which in the initial state of the injection device is held relative to the housing and which at least partly covers the needle assembly, the cover being adapted for movement relative to the housing, wherein the injection device defines an unsealing member which is adapted to cause the film seal to change from a sealing state into an unsealing state by relative movement between the needle assembly and the unsealing member, and wherein relative movement between the cover and the housing causes the film seal to change from the sealing state to the unsealing state.

According to the aspect identified above, by configuring the device with a cover which may form part of the packaging of the device and which is moved relative to the injection device prior to use, by utilizing the relative movement of one or more parts of the packaging when the packaging is opened by the user gaining access to the device, the mechanism for mounting the needle can be implemented in the packaging in which the device is delivered.

The said initial state of the injection device may correspond to a storage state where the cover is attached relative to the housing of the injection device for enabling proper long-term storage conditions for the injection device.

In the storage state of the injection device, the cover may be held relative to the housing in a first relative position wherein the cover at least partly covers the needle assembly. Upon movement between the cover and the housing from the first relative position to a second relative position the film seal is caused to shift from the sealing state to the unsealing state. Hereby the injection device is shifted into a ready-to-administer state. During the relative movement between the cover and the housing from the first relative position to the second relative position, the cover may remain continuously coupled with the housing. Hence, from the storage state to the ready-to-administer state the cover is not detached relative to the housing.

The cover may be connected to the housing of the injection device by a coupling mechanism which defines a pre-defined movement between the cover and the housing from the storage state to the state where the seal has been shifted into the unsealing state.

In said unsealing state, the injection device has been shifted into a ready-to-administer state. In the ready-to-administer state, the cover may be moved further relative to the housing for enabling the needle container to be removed from the injection needle.

The injection device may be configured to enable manual actuation of the piston driver to drive the piston towards the outlet subsequent to the cover being operated for changing the film seal from the sealing state to the unsealing state. In some forms, the injection device is so configured that upon manual actuation the user presses forward the piston driver during dose expelling operation. In other forms, the injection device is so configured that a pre-tensed spring drives forward the piston driver upon manual actuation of an activation member. Non-exhaustive examples of such activation member may be an activation button, a sleeve movably arranged relative to the housing, such as a needle sleeve or a needle shield. In some forms, the manual actuation of the piston driver is prevented until the injection device has been shifted into the ready-to-administer state whereupon actuation is enabled. In other forms, the manual actuation of the piston driver is prevented until the needle container is removed from the injection needle whereupon actuation is enabled.

In some embodiments, the needle container defines a sealed chamber wherein the injection needle is completely accommodated. The needle container may incorporate a body having a cup shaped form and defining a single sealed opening, wherein the single sealed opening is sealed by the film seal when the injection device is in the storage state.

The film seal of the needle assembly may take form of a planar film, such as a paper seal which is adhered or otherwise sealingly attached along a rim section of an opening of the needle container. The needle assembly may form a standard needle package for use in connection with injection pens which are commonly being used for administering medicaments for the treatment of diseases such as diabetes. Exemplary needle assemblies suitable for use in connection with the above aspect are disclosed in EP 279583 A2, WO 96/02290 A2 and WO 2004/004812 A1.

In some embodiments, the cover moves from a first position to a second position to cause the needle assembly and the unsealing member to move relative to each other along the main axis to cause the film seal to change from the sealing state to the unsealing state. In such embodiment, the movement of the cover from the first position to the second position may be different than a purely axial movement, such as by a purely rotational movement, a combined rotational and axial movement, or a sequence of axial and rotational movements.

In some embodiments, the front and rear needle defines a common axis. In the storage state of the device the common axis may be identical with a longitudinal axis of the cartridge, i.e. the main axis. In other forms, in the storage state the common axis is not identical with the longitudinal axis of the cartridge. In such a configuration, the common axis and the longitudinal axis are brought into alignment when the cover and the housing is moved relatively from the first relative orientation to the second relative orientation.

The above mentioned coupling mechanism defining the pre-defined movement between the cover and the housing may in some embodiments involve a rotational movement of the cover relative to the housing. This may be provided by a mechanism which transfers the force exerted by the user for operating the cover into a larger force for changing the film seal from the sealed state to the unsealed state. Thereby safe and effective unsealing of the film seal may be carried out where the film seal is removed or ruptured in a consistent way. In addition, such solution enables use of standard components such as standard needle assemblies and standard cartridges which provides for manufacture in a cost-effective manner.

In some forms the cover moves from a first position to a second position to cause the film seal to change from the sealing state to the unsealing state and wherein a force exerted by the user for operating the cover relative to the housing is transformed to a force of greater magnitude for effecting relative movement between the needle assembly and the unsealing member along said main axis.

In some embodiments, the cover forms a cap which attaches to or is being held relative to a distal end of the housing of the injection device when the device is in the initial state.

The cap and the housing may be configured to form a track and groove connection. In such configuration, a relative rotational movement between the cap and the housing is transformed into a linear movement defined by means of said track and groove connection for causing relative axial movement between the needle assembly and the unsealing member.

In some forms, the injection device includes a pre-stressed spring which releases upon operation of the cap relative to the housing, wherein the spring, when released, drives the needle assembly and the unsealing member relative to each other for changing the film seal from the sealing state to the unsealing state.

In some forms, the cover at least in part forms a packaging which in the storage state of the injection device accommodates the housing of the injection device. The cover may define a first cover section which swivels relative to the housing along a second axis, where the second axis is substantially orthogonal to the main axis.

In some forms, the first cover section forms a lever arm which upon operation causes the needle assembly and the unsealing member to move relative to each other.

In addition to the first cover section, the cover may further define a second cover section wherein the first and second cover sections forms cooperating shells for accommodating the housing and the needle assembly. The first and the second cover section may be configured to rotate relative to each other around a third axis. The second axis and the third axis may in some embodiments define parallel axes.

In some embodiments, relative movement between the cover and the housing further causes the rear section of the injection needle to pierce the cartridge septum for establishing fluid communication with the interior of the cartridge.

In still other embodiments, the cover is configured for being separated from the housing subsequent to the cover being operated for changing the film seal from the sealing state to the unsealing state but prior to manual actuation of the piston driver for driving the piston towards the outlet. The cover may in further embodiments be so configured that when the cover is separated from the housing, the needle container is automatically separated from the injection needle whereby access to the front needle is enabled. The cover may in some forms be configured for being separated relative to the housing of the injection device after the injection device has been brought into the ready-to-administer state. In some forms the needle container is mounted within the cover so that the needle container is removed from the injection needle as the cover is separated from the housing.

In some embodiments, the unsealing member may be formed as a member held in the housing of the injection device, either as a separate member or as a part formed by the housing, or alternatively, the cartridge itself may define the unsealing member. The unsealing member may include features enabling a consistent unsealing, e.g. for obtaining safe and effective rupturing or peeling of the film seal from the needle container, by including one or more cutting surfaces with sharp or point-like features or the like.

Some variants may use cartridges made of glass. Other embodiments may incorporate a cartridge being made of a synthetic resin or the like. In addition, some embodiments may use a cartridge having a cartridge body which at the same time performs as a housing of the injection device.

The housing of the device may in some embodiments be formed to define a distal end and a proximal end. In some embodiments, the overall shape of the injection device may be formed to exhibit a pen-shape.

The device may in some embodiments be formed as a disposable (single use) device which in one form may be adapted to deliver a single dose of a medicament for subsequent disposal. Such device may have a medicament cartridge irremovably accommodated inside the housing. In some forms, the device may be adapted to dispense either a pre-determined fixed dose of medication through an expelling operation. In other forms, the device may be configured to enable the setting of the size of a dose intended for subsequent injection during an expelling operation.

As used herein, the term "distal end" of the injection device or a component thereof may refer to that end of the device or the component which is closest to the dispensing end of the device. The term "proximal end" of the injection device or a component thereof may refer to that end of the device or the component which is furthest away from the dispensing end of the device.

As used herein, the term "medicament" is meant to encompass any medicament-containing flowable drug capable of being passed through a delivery means such as a hollow needle or cannula in a controlled manner, such as a liquid, solution, gel or fine suspension. Also lyophilized drugs which prior to administration are dissolved into a liquid form is encompassed by the above definition. Representative medicaments includes pharmaceuticals such as peptides, proteins (e.g. insulin, insulin analogues and C-peptide), and hormones, biologically derived or active agents, hormonal and gene based agents, nutritional formulas and other substances in both solid (dispensed) or liquid form.

DETAILED DESCRIPTION OF THE INVENTION

The invention will now be described in further detail with reference to the drawings in which:

FIG. 1a shows a cross sectional view of a first embodiment of an injection device 100 and a needle assembly in a packaging 200 according to the invention, in an initial storage state, FIGS. 1b-1f show cross sectional views of different operating stages during unpackaging of the injection device 100 shown in FIG. 1a, FIGS. 2a-2g show different operating stages of a second embodiment of an injection device 100' accommodating a needle assembly 150' and having a cap member 170', the views showing side views of a sectional cut through housing 101', FIGS. 3a-3g show cross sectional views of the second embodiment of the injection device 100' in different operating stages corresponding to operating stages shown in FIGS. 2a-2g, FIGS. 4a-4e show side views of different operating stages of a third embodiment of an injection device 100" accommodating a needle assembly 150" and having a cap member 170", and FIGS. 5a-5e show cross sectional views of the third embodiment of an injection device 100", the views of the different operating stages correspond to the operating stages shown in FIGS. 4a-4e.

FIG. 1a shows a cross sectional view of a first embodiment of a medical injection device 100 for medically injecting a pre-determined amount of a liquid medicament. FIG. 1a shows the injection device 100 in a storage condition. The depicted embodiment shows a disposable device which is adapted to administer a fixed dose of medicament upon activation for subsequent disposal. The embodiment shows an injection device in the form of an auto-injector which provides automatic injection of medicament from a standard cartridge 120. The cartridge 120 has a piston arranged internally which is arranged slideably along a central axis of the cartridge for being driven towards an outlet of the cartridge. A piercable septum seals the outlet of cartridge 120 prior to use thereof, the septum being adapted to be pierced by an injection needle for establishing fluid communication with the medicament of the cartridge.

FIG. 1a further shows a needle assembly 150 comprising a needle container 151 accommodating a double pointed injection needle 152, 153. The injection needle includes a needle cannula 153 having a front and a rear needle section and a needle hub 152 which is used for connecting the injection needle to the main part of the injection device 100. The needle container 151 has an proximally facing opening which is sealed by a sterility seal 155, such as a planar film seal, for example in the form of a paper seal which is attached along a rim section of an opening of the needle container 151. The shown needle assembly 150 forms a standard needle package for use in connection with injection pens which are commonly being used for administering medicaments for the treatment of diseases such as diabetes.

In FIG. 1a, a cap member 170 is depicted that cooperates with housing 101 and is adapted to slide axially relative to housing 101. With the device in the storage condition, the cap member 170 holds the complete needle assembly with the film seal intact.

FIG. 1a further shows a packaging in the form of a cover 200 having cover sections 201 and 202. In the storage state of the device, the cover 200 holds the needle assembly 150 separate from the main part of the injection device 100 and hence separate from the cartridge 120. The film seal 155 is still attached to needle container 151 hence providing storage of the injection needle in the sterilized state. In the storage state, internally in cover 200, the needle assembly 150 and the main part of the injection device 100 are arranged such that the sterility seal 155 opposes an unsealing member 115 associated with the cartridge septum of cartridge 120.

Figure 1E:
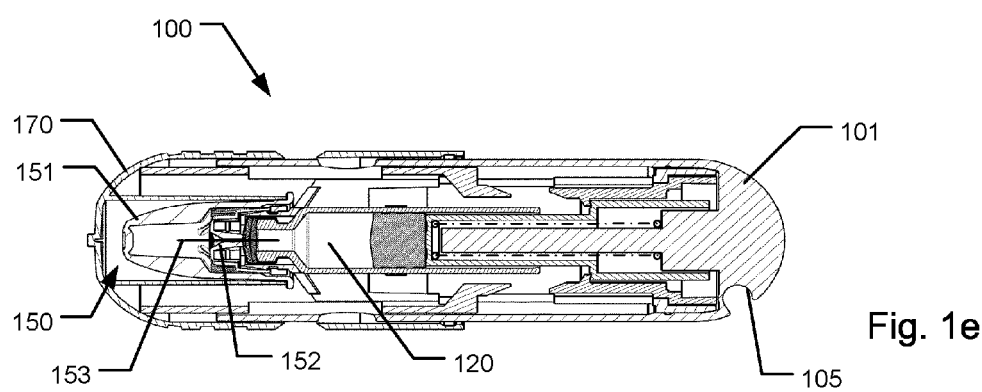
Figure 1F:
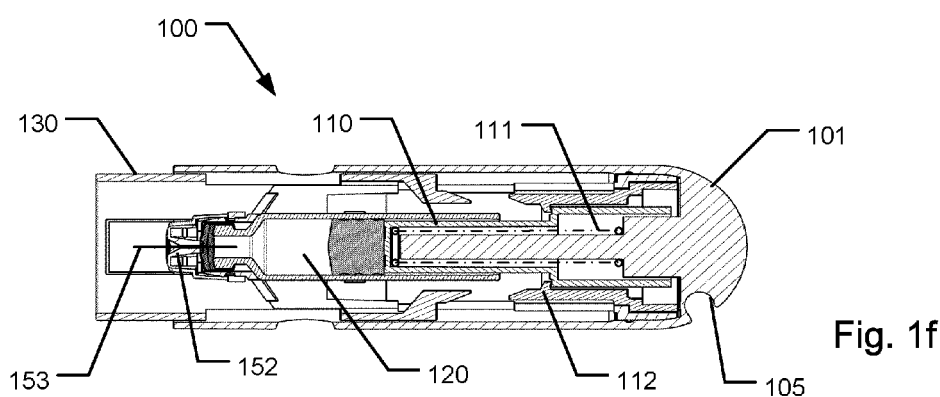

For a comparison of the injection device 100 in the ready to use state, i.e. where the injection needle 153 is attached to the cartridge 120, reference is made to FIG. 1f.

In FIGS. 1a through 1d the drawings show the operation of unsealing the needle container for enabling connection of the injection needle 152/153 with the injection device 100 by moving the upper cover section 201 with respect to the bottom cover section 202 from the fully closed configuration to the fully open configuration.

As shown in FIG. 1b, cover sections 201 and 202 connects by means of a first swivel joint so that the top cover section 201 may be rotated approximately 180 degrees relative to the bottom cover section 202 around a first swivel joint 204 from the fully closed configuration to the fully open configuration. Top cover section 201 further forms an axle stub 205 which cooperate with a recess 105 in housing 101 of injection device 100. In the depicted embodiment the top cover 201 defines an approximate "L" shaped member having a relatively long first arm and a relatively short second arm arranged approximately 90 degrees apart. The first swivel joint 204 is disposed where the two arms intersect and the axle stub 205 is arranged at the free end of the second arm. The bottom cover section 202 is adapted to hold the cap member 170 so that the cap member 170 and the housing 100 cannot be further separated. Due to the geometry of the top cover section 201, with the layout of first swivel joint and axle stub 205, the top cover 201 forms a lever arm which when top cover 201 is initially opened it acts to push housing 101 towards the cap member 170, i.e. causing the device formed by housing 101 and 170 to become shorter, cf. FIG. 1b and FIG. 1c.

As the housing 101 is moved relatively to cap member 170 the unsealing member 115 is pushed to protrude through film seal 155 enabling the rear section of the injection needle 153 to connect to the cartridge 120, i.e. by penetrating the septum of the cartridge. In the shown embodiment, this occurs shortly after the top cover has moved past the position shown in FIG. 1c. Due to the lever arm construction of the cover sections, a considerable force may be provided to enable the film seal to be securely penetrated by the unsealing member. When the top cover 201 is moved further towards the fully open position, the assembly formed by housing 101 and cap member 170 is retracted a short distance and lifted from the bottom cover section 202. Due to the joint formed by axle stub 205 and recess 105 forming a detachable connection, when the cover sections are positioned in their open configuration, the housing 101 and cap member 170 of the injection device 100 may be easily separated from the casing sections 201 and 202. In this state, as shown in FIG. 1e, the device 100 is prepared for use (ready-to-administer condition). After initially removing the cap member 170 the device is in a ready-to-injection condition (see FIG. 1f). As the needle container 151 is attached to the cap member 170, separating the cap member 170 from the housing 101 causes the needle container 151 to separate from the main part of the injection device 100 as well. In the depicted embodiment, the cap member 170 forms a security cap. In other embodiments, the cap member 170 may be omitted. In such embodiments, the bottom cover section 201 may be adapted to initially hold the needle container 151 such that separating the device 100 from the two casing sections 201 and 202 causes the needle container 151 to automatically separate from the main part of the injection device 100.

The ready-to-inject state of the injection device 100 where the cap member 170 has been removed is shown in FIG. 1f. As noted above the injection device may be formed as an auto-injector which for exemplary purposes will be shortly described. In the depicted embodiment, the piston driver 110 is biased by a pre-stressed spring 111. Before actuation, the piston driver 110 is held in a retracted position due to being retained by retaining ledges of a retaining member 112. A needle shield 130 is initially positioned in an extended position (biased by a not shown spring) so as to cover the front section of the needle 153. When the injection device is positioned at an injection site, by forcing the device 100 against the skin, the needle shield 130 is forced backwards. The needle shield 130 includes activating surfaces adapted to cooperate with the retaining member 112 such that when the needle shield has been pushed sufficiently proximally for the front section of the injection needle 153 to be inserted into the skin of the patient, the retaining member 112 releases the piston driver 110. Due to the energy stored in the pre-stressed spring 111, the piston driver 110 is driven forward to expel the pre-defined dose. After dose injection, the injection device 100 may be withdrawn from the skin, and the injection device may be discarded after re-positioning the cap member 170 and/or the cover sections 201 and 202.

In the shown embodiment the injection needle 152/153 is attached to the main part of the injection device 100 by means of a purely translation movement involving no rotation. The needle mounting surfaces of the needle hub 152 and/or the mounting surface of the injection device (un-referenced) may be formed to allow connection by a non-rotational relative linear movement for example by designing the needle hub and/or the mounting surface to obtain a snap connection. As an example, the protrusions of the needle hub of the injection needles shown in WO 2004/004812 A1 can be used as one part of a snap lock to lock the injection needle to the injection device, thus eliminating the need for a rotating movement during mounting of the needle.

As discussed above, the film seal 155 is broken as the unsealing member 115 protrudes through the opening formed in needle container 151. Alternatively, or in addition, the pull tab formed in the film seal of conventional needle containers may be attached to the top cover section 201 by means of a peel member 206 formed to protrude from the inner surface of top cover section 201 towards the film seal 155 of the needle assembly 150, see FIGS. 1a and 1.b. As the top cover section 201 is initially rotated relative to bottom cover section 202, the peel member 206 peels off the film seal 155 by moving the film seal in a direction approximately transversely to a centre axis of the needle assembly 150. Hence, the peel member 206 may fully or partly peel off the film seal from the rim of the needle container 151 to enable easy penetration of the unsealing member 115 or alternatively allow for the cartridge 120 to protrude directly into the interior of the needle container 151.

Depicted in FIGS. 2a-2g and FIGS. 3a-3g a second embodiment of an injection device 100' is shown. As for the first embodiment, the various drawings show the injection device 100' in different stages during unsealing and mounting of an injection needle 152'/153' relative to the main part of the injection device 100'. FIGS. 2a through 2g show side views of the device 100' with a sectional cut through housing 101' to allow inspection of a track and groove connection between the housing 101' of the injection device and a cover defining a cap member 170' which attaches to a distal end of the injection device 100'. FIGS. 3a through 3g are centre cross sectional views of the injection device 100' corresponding to the states shown in FIGS. 2a through 2g respectively.

The second embodiment of the injection device 100' shows a manual injector having an actuating button 103' arranged at the proximal end of housing 101' which allows the piston of cartridge 120' to be driven manually for expelling the contents of the cartridge. In the storage state of the device shown in FIGS. 2a and 3a, the cap member 170' holds a needle assembly 150' which generally correspond to the needle assembly 150 shown in the first embodiment. The cap member 170' serves as a tool for allowing the film seal 155' of the needle assembly 150' to be changed from the sealed state to an unsealed state by rotating the cap member 170' relatively to housing 101'. To facilitate ergonomic operation, in particular for users having limitations in dexterity, the cap member 170' includes a pair of wings which are easily gripped by one hand while the housing 101' may be firmly gripped by the other hand.

As noted above a track and groove connection is formed between cap member 170' and housing 101'. This track and groove connection defines the relative motion between the two components. In the shown embodiment, the cap member 170' has a proximal section which is inserted internally in a distal part of housing 101'. A protrusion 102' protrudes radially inwards from housing 101' to cooperate with a track 171' formed in an exterior part of the cap member 170'. The cap member may have an arrow indicator 172' formed on a visible part thereof as shown on the drawings. The arrow indicator 172' is indicative of the intended way of operation of the cap member 170' relative to housing 101'.

Figure 3A:
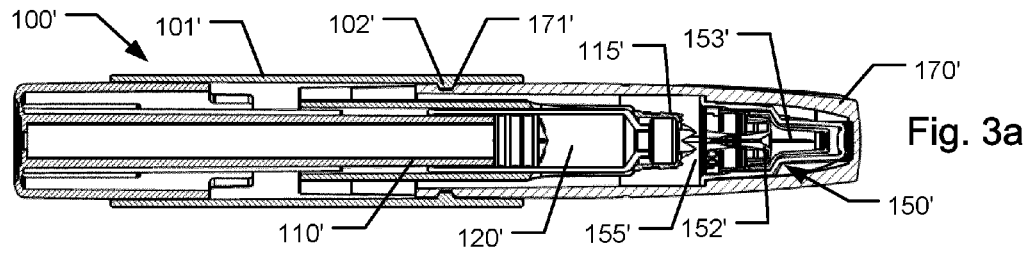
Figure 3B:
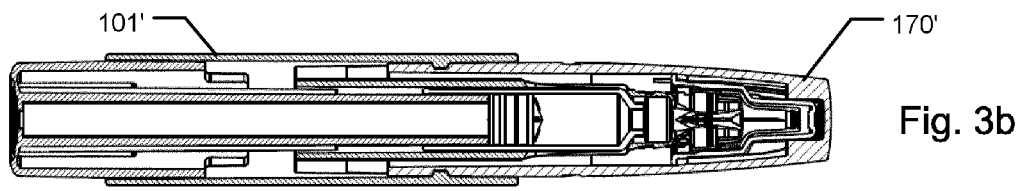
Figure 3C:
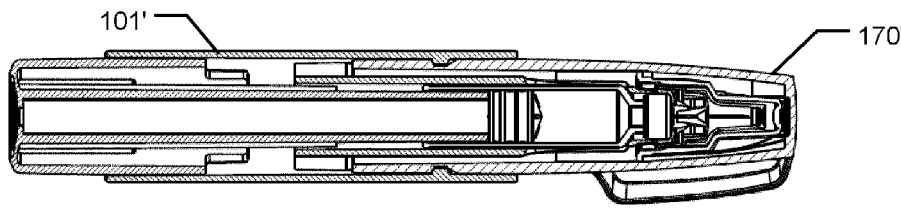
Figure 3D:
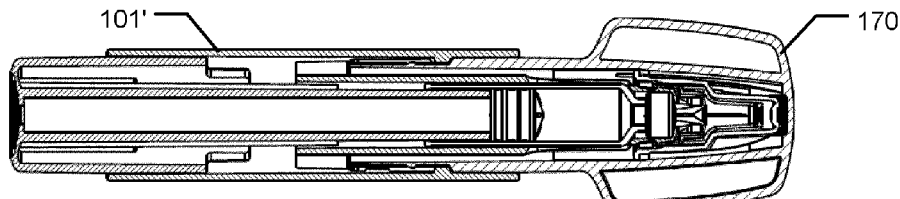
Figure 3E:
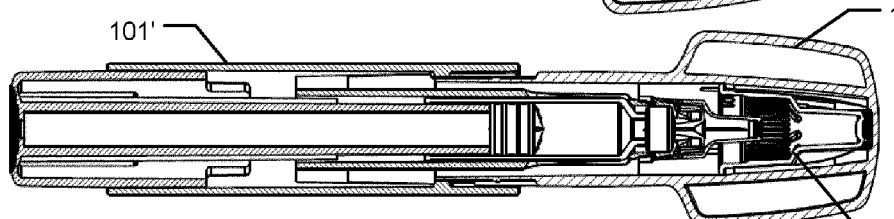

As shown in FIG. 3a which shows the device in the initial storage condition, the needle assembly is arranged separated from the cartridge 120' and separated from unsealing member 115'. Hence the injection needle 152'/153' is stored in a sterile condition due to the film seal 155' being intact.

The track 171' has a shape which roughly corresponds to the shape of the arrow indicator 172'. In the shown embodiment, the cap member 170' is initially rotated which induces an axially movement of cap member 170' in the proximal direction (shown in FIGS. 2a-2d and 3a-3d). During this rotation, the assembly formed by housing 101' and cap member 170' is made shorter. Due to the relative axial motion between cap member 170' and housing 101', the needle container 151' is pressed towards the unsealing member 115'. Due to the force exerted on the cap member 170' by the rotational movement is transferred to a larger force in the axial direction the unsealing member protrudes relatively easy into the cavity formed by the needle container 151' thereby rupturing the film seal 155' and allowing the rear section of the injection needle 153 to penetrate the cartridge septum (see FIG. 3d).

Figure 2A:
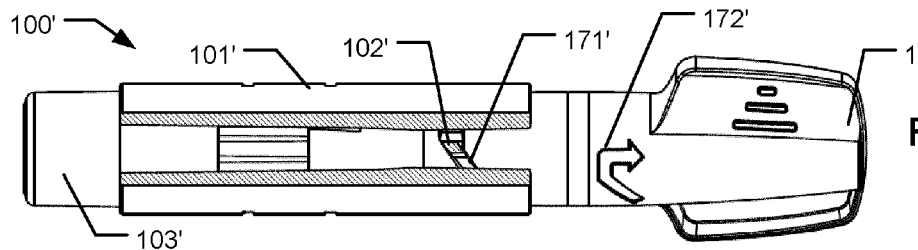
Figure 2B:
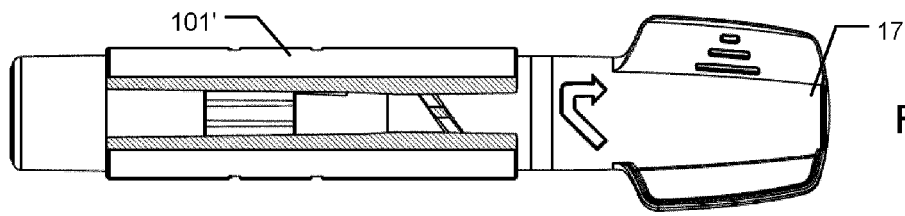
Figure 2C:
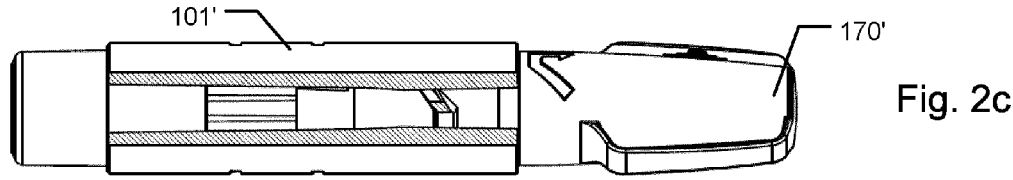
Figure 2D:
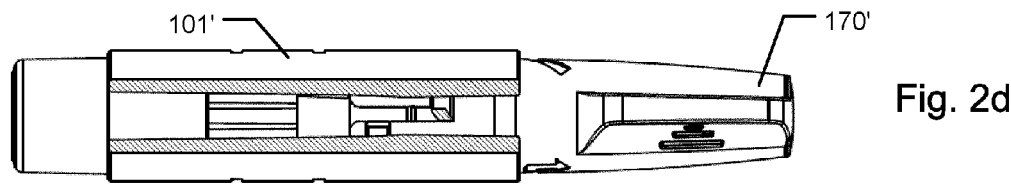
Figure 2E:
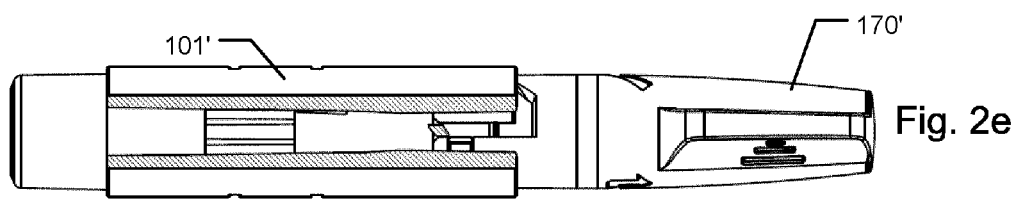
Figure 2F:
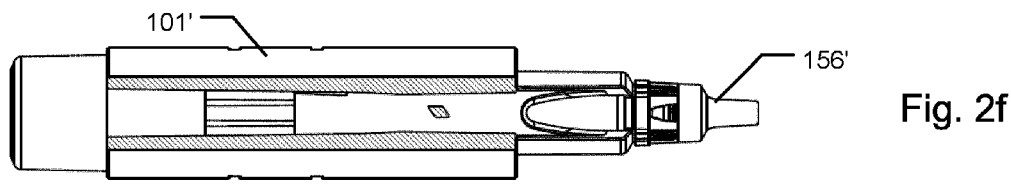
Figure 2G:
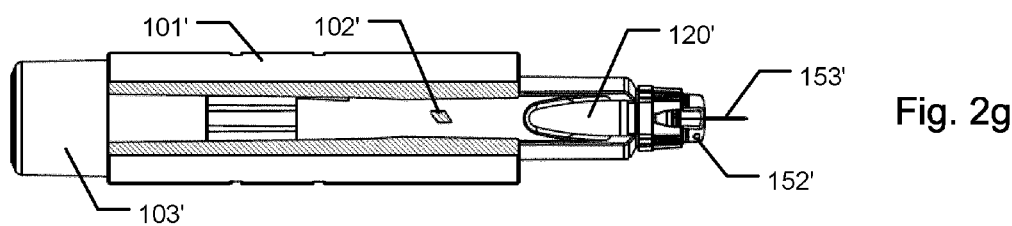
Figure 3F:
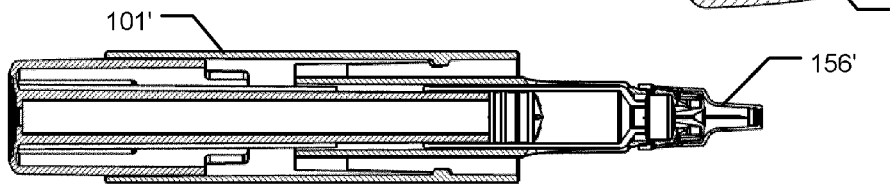
Figure 3G:
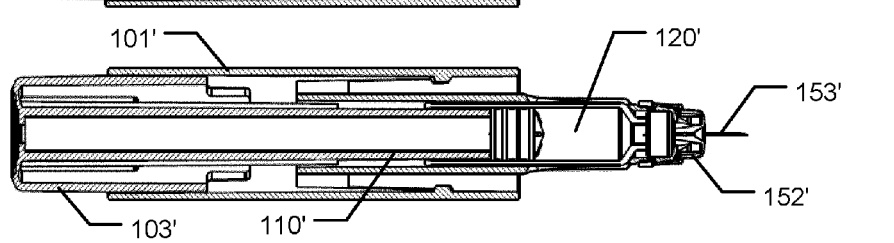

The track 171' defines that further rotation is not possible. However, due to a segment of track 171' extending in the axial direction, the cap member 170' may be moved in the distal direction thereby separating the cap member 170' from the housing 101' of injection device 100' (see FIGS. 3e and 3f). In the shown embodiment, the cap member 170' firmly grips the needle container 151' which thereby is withdrawn from the housing 101' as the cap member 170' is removed. As shown in FIGS. 2f and 3f, an inner cap 156' protects the needle before administration is to be performed. After removal of inner cap 156' the injection device 100' is in a ready-to-inject condition (see FIGS. 2g and 3g).

As in the first embodiment, the needle hub 152' and a mounting surface of the injection device 100' may form a snap connection. Alternatively, the connection may be provided as a threaded connection or as a bayonet connection. The track 171' may be formed to allow the rotational coupling of such threaded connection or bayonet connection so that the rotation of cap member 170' relative to housing 101' ensures the correct attachment between the needle hub 152' and the needle mounting surface of the device.

After administration, the cap member 170" may be re-attached to the housing 101" for safe disposal of the used injection device 100".

FIGS. 4a-4e and FIGS. 5a-5e shows a third embodiment of an injection device 100". As for the first and second embodiments, the various drawings show the injection device 100" in different stages during unsealing and mounting of an injection needle 152"/153" relative to the main part of the injection device 100". FIGS. 4a through 4e show external side views of the device 100" and a cover defining a cap member 170" which attaches to a distal end of the injection device 100". FIGS. 5a through 5e are centre cross sectional views of the injection device 100" corresponding to the states shown in FIGS. 4a through 4e respectively.

The third embodiment of the injection device 100" shows an auto-injector having an actuating button 103" arranged at the proximal end of housing 101" configured for being manually actuated. Upon manual actuation the device is triggered allowing the piston of cartridge 120" to be driven automatically by a pre-stressed spring for expelling the contents of the cartridge. Although only schematically described, the shown third embodiment of the auto-injector involves auto-insertion of the injection needle at an injection site when the injection device 100" is triggered. This occurs by moving the cartridge 120" with the injection needle 152"/153" attached in a distal direction internally in housing 101".

Figure 4A:
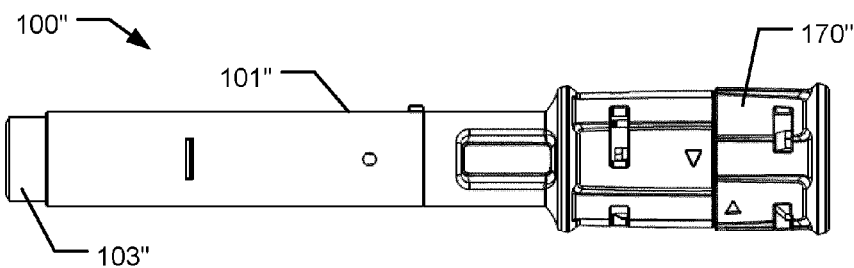
Figure 4B:
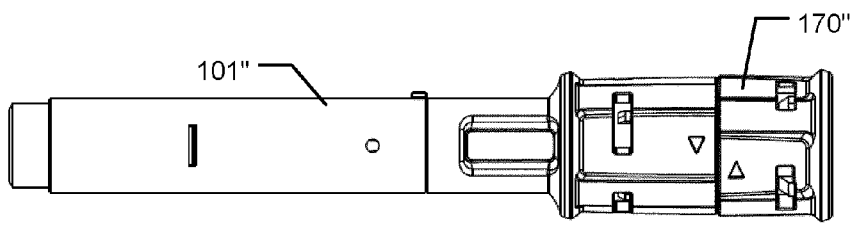
Figure 5A:
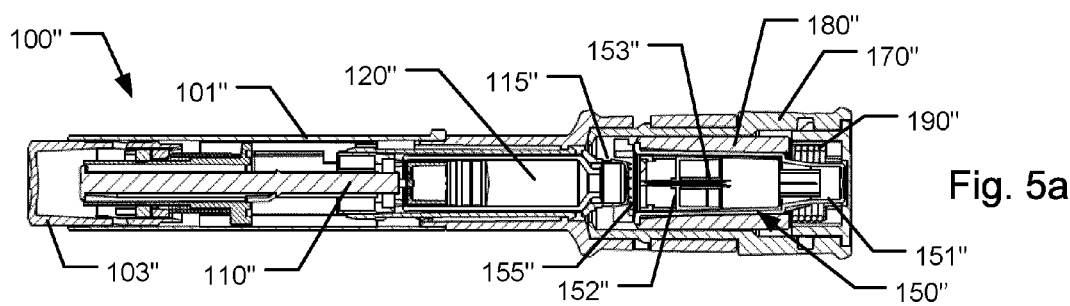
Figure 5B:
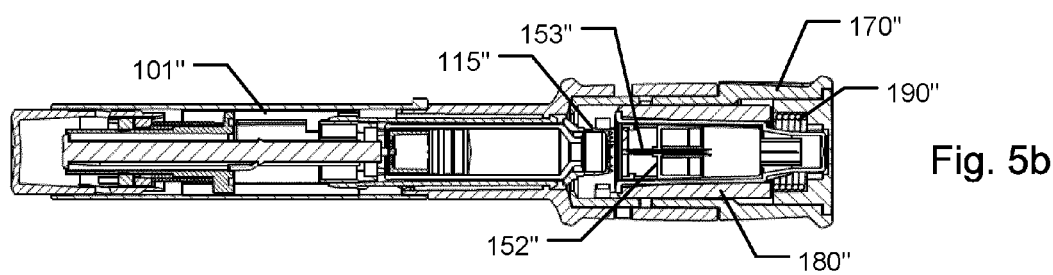

In the storage state of the device shown in FIGS. 4a and 5a, the cap member 170" holds a needle assembly 150". The needle assembly may be of the kind shown in WO 03/045480 A1 which discloses a needle having a needle shield being biased by a spring element for maintaining the injection needle hidden prior to use and which locks in the extended position after use. As shown in FIG. 5a which shows the device 100" in the initial storage condition, the needle assembly 150" is arranged separated from the cartridge 120" and separated from unsealing member 115". Hence the injection needle 152"/153" is stored in a sterile condition due to the film seal 155' being intact.

A not shown connection between cap member 170" and housing 101" defines the two parts to be initially rotated. After the end of the rotation, the cap member 170" may be removed from housing 101".

The cap member 170" includes a mechanism for providing the unsealing action for the film seal 155" of the needle assembly 150" upon rotation of cap member 170" relative to the housing 101". The mechanism includes a pre-stressed spring 190" dedicated to the unsealing action for removing and/or penetrating and/or rupturing the film seal of the needle assembly 150". The distal end of the pre-stressed spring 190" is held by the cap member 170" whereas the proximal end of the spring 190" acts upon an axially movable member 180". The axially movable member 180" is mounted relative to the needle container 151".

Figure 4C:
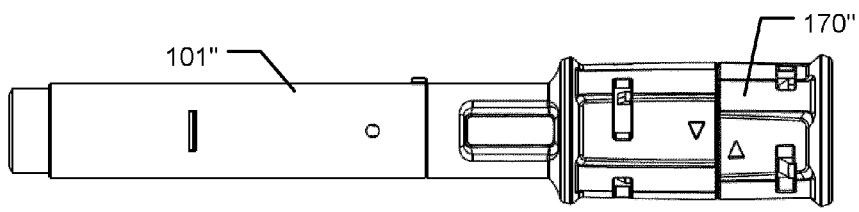
Figure 5C:
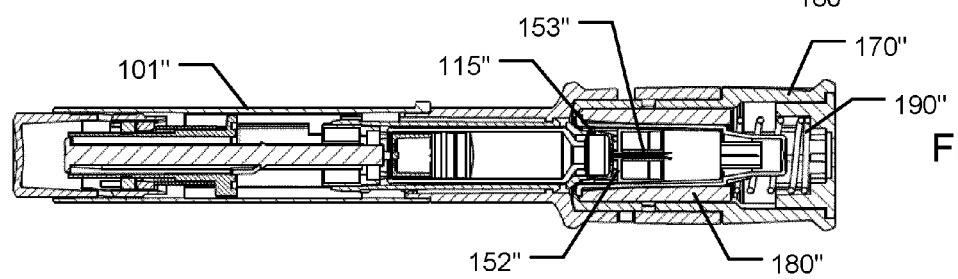

Upon rotation of cap member 170" relative to housing 101" from a first position shown in FIGS. 4a and 5a to a second position shown in FIGS. 4c and 5c the axially movable member 180" is released from an initial distal position. Due to the spring force of spring 190" the axially movable member 180" is forced in the proximal direction which presses the needle assembly 150" in the proximal direction. The spring force thereby forces the unsealing member 115" to enter into the cavity formed by the proximal end of the needle container 151" thereby changing the film seal 155" from the sealed state to the unsealed state. By this mechanism a relatively low force required for rotating the cap member 170" relative to the housing 101" is transformed into a relatively high force in the axial direction. By choosing the spring constant of the spring 190" and the point of impact, the pre-defined impact needed for the unsealing action may be optimally ensured. In this embodiment, the movement of the needle assembly 150" relative to the housing 101" also incorporates needle penetration into the cartridge septum.

Figure 4D:
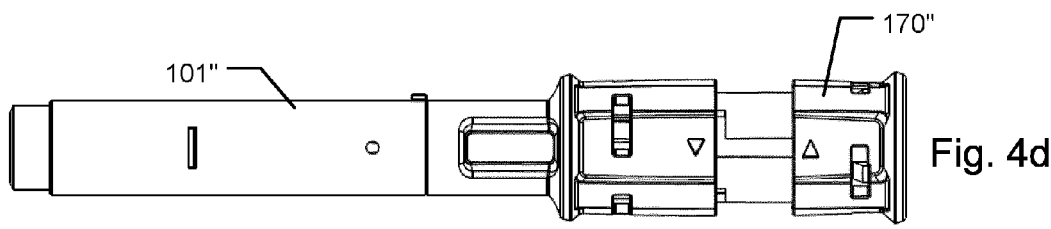
Figure 4E:
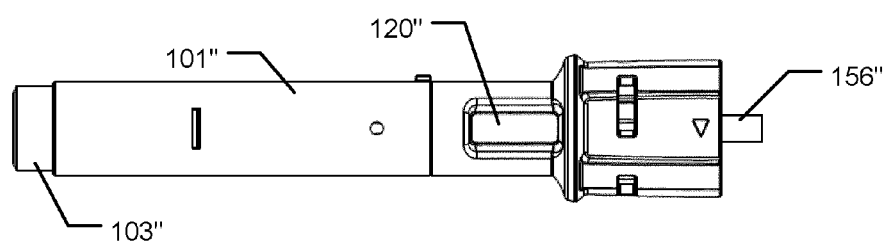
Figure 5D:
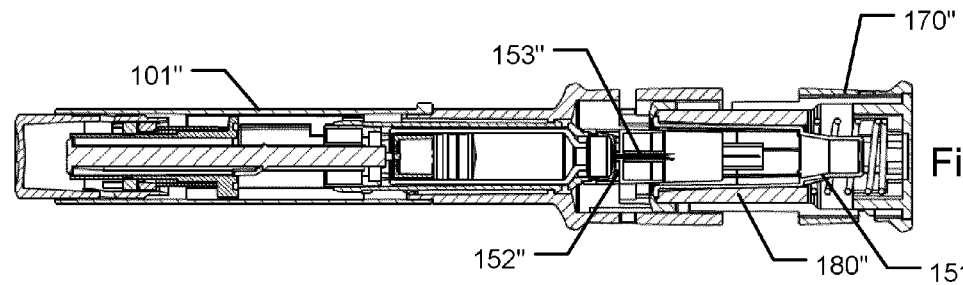

As shown in FIGS. 4d and 5d, the cap member 170" may subsequently to the unsealing action be moved in the distal direction thereby separating the cap member 170" from the housing 101" of injection device 101" (see FIGS. 4e and 5ef). In the shown third embodiment, the cap member 170" and the axially movable member 180" holds the needle container 151" which thereby is withdrawn from the housing 101" as the cap member 170" is removed.

Figure 5E:
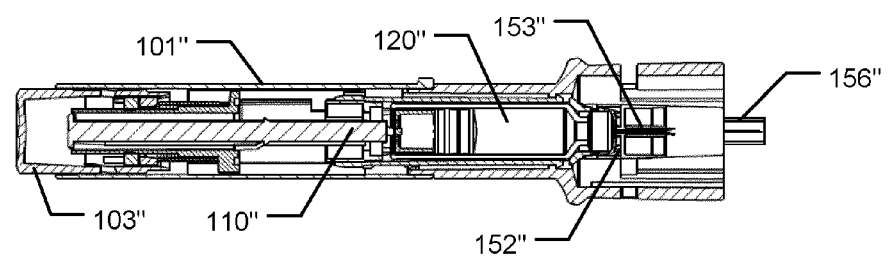

As shown in FIGS. 4e and 5e, a needle shield 156" protrudes slightly from the distal end of the housing 101". This needle shield automatically retracts relative to the housing when the injection device 100" is pressed against an injection site. Hence, FIGS. 4e and 5e show the injection device 100" in the ready-to-inject condition.

After administration, the cap member 170" may be re-attached to the housing 101" for safe disposal of the used injection device 100".

It should be noted that in the above described embodiments, the type of injection devices shown serve mainly as exemplary embodiments for explaining the function of the needle unsealing procedure. In the shown embodiments, injectors having auto-injection functionality and manual injectors are used but these may be interchanged. In addition, in alternative embodiments, other types of injectors having higher or lower levels of automation may be used, e.g. injectors having auto-insertion or auto-retraction of the needle as well as manual insertion and retraction of the injection needle. In the injectors, the cartridge accommodated in the device may be fixedly attached inside the housing or may be mounted slideably relative to the housing.

Some preferred embodiments have been shown in the foregoing, but it should be stressed that the invention is not limited to these, but may be embodied in other ways within the subject matter defined in the following claims.

The invention claimed is:

1. An injection device comprising:
a housing,
a cartridge arranged relative to the housing and defining a main axis, the cartridge comprising an outlet covered by a cartridge septum adapted to be pierced by an injection needle for establishing fluid communication with a cartridge interior and comprising a piston which is driveable along the main axis towards the outlet,
a piston driver for engaging the piston and capable of being actuated for driving the piston in a distal direction towards the outlet,
a needle assembly arranged at the distal end of the housing, the needle assembly comprising the injection needle having front and rear sections for respectively penetrating skin of a subject user and for piercing the cartridge septum, the needle assembly further comprising a needle container accommodating the injection needle, the needle container having an opening which in a storage state of the injection device is sealed by a film seal for maintaining the injection needle in a sterile condition, and
a cover arranged relative to the housing and configured for relative movement, wherein, in the storage state of the injection device, the cover is held relative to the housing in a first relative orientation wherein the cover at least partly covers the needle assembly,
wherein the cover at least in part forms a packaging which in the storage state of the injection device accommodates the housing of the injection device, and the cover defines a first cover section which swivels relative to the housing along a second axis, the second axis being substantially orthogonal to the main axis,
wherein the injection device defines an unsealing member which is adapted to cause the film seal to change from a sealing state into an unsealing state by relative movement between the needle assembly and the unsealing member, wherein the first cover section forms a lever arm which upon operation causes the needle assembly and the unsealing member to move relative to each other, and
wherein relative movement between the cover and the housing from the first relative orientation to a second relative orientation causes the film seal to change from the sealing state to the unsealing state for shifting the injection device into a ready-to-administer state, the cover being continuously coupled with the housing during said relative movement between the cover and the housing from the first relative orientation to the second relative orientation.

2. An injection device as in claim 1, wherein the needle container defines a sealed chamber wherein the injection needle is completely accommodated, the needle container forming a body having a cup shaped form and defining a single sealed opening, wherein the single sealed opening is sealed by said film seal when the injection device is in said storage state.

3. An injection device as in claim 1, wherein the injection device is configured to enable manual actuation of the piston driver to drive the piston towards the outlet subsequent to the cover being operated for changing the film seal from the sealing state to the unsealing state.

4. An injection device as in claim 1, wherein the cover moves from a first position to a second position to cause the needle assembly and the unsealing member to move relatively to each other along said main axis to cause the film seal to change from the sealing state to the unsealing state and wherein the movement of the cover from the first position to the second position is different than a purely axial movement.

5. An injection device as in claim 1, wherein the cover moves from a first position to a second position to cause the film seal to change from the sealing state to the unsealing state and wherein a force exerted by the user for operating the cover relative to the housing is transformed to a force of greater magnitude for effecting relative movement between the needle assembly and the unsealing member along said main axis.

6. An injection device as in claim 1, wherein the cover forms a cap which attaches to the distal end of the housing when the injection device is in the storage state.

7. An injection device as in claim 6, wherein the cap and the housing forms a track and groove connection and wherein a relative rotational movement between the cap and the housing is transformed into a linear movement defined by said track and groove connection for causing relative axial movement between the needle assembly and the unsealing member.

8. An injection device as in claim 6, wherein the injection device includes a pre-stressed spring which releases upon operation of the cap relative to the housing, wherein the spring, when released, drives the needle assembly and the unsealing member relative to each other for changing the film seal from the sealing state to the unsealing state.

9. An injection device as in claim 1, wherein the cover further defines a second cover section wherein the first and second cover sections forms cooperating shells for accommodating the housing and the needle assembly.

10. An injection device as in claim 1, wherein relative movement between the cover and the housing further causes the rear section of the injection needle to pierce the cartridge septum.

11. An injection device as in claim 1, wherein the cover is configured for being separated from the housing subsequent to the cover being operated for changing the film seal from the sealing state to the unsealing state but prior to actuation of the piston driver for driving the piston towards the outlet.

12. An injection device as in claim 11, wherein the cover is configured for removing the needle container from the injection needle as the cover is separated from the housing.

* * * * *